United States Patent
Magistrali et al.

(10) Patent No.: US 11,400,041 B2
(45) Date of Patent: Aug. 2, 2022

(54) USE OF COMPOSITIONS COMPRISING DESTRUCTURIZED STARCH IN A COMPLEXED FORM AS ABRASIVES AND/OR STRUCTURING AGENTS

(71) Applicant: Novamont S.p.A., Novara (IT)

(72) Inventors: Paolo Magistrali, Novara (IT); Nicola Marini, Varallo Pombia (IT); Ioanna Petrakou, Novara (IT)

(73) Assignee: NOVAMONT S.P.A., Novara (IT)

( * ) Notice: Subject to any disclaimer, the term of this patent is extended or adjusted under 35 U.S.C. 154(b) by 663 days.

(21) Appl. No.: 16/069,890

(22) PCT Filed: Jan. 18, 2017

(86) PCT No.: PCT/EP2017/050972
§ 371 (c)(1),
(2) Date: Jul. 13, 2018

(87) PCT Pub. No.: WO2017/125430
PCT Pub. Date: Jul. 27, 2017

(65) Prior Publication Data
US 2019/0021979 A1    Jan. 24, 2019

(30) Foreign Application Priority Data

Jan. 19, 2016 (IT) .......................... 102016000004478

(51) Int. Cl.
| | |
|---|---|
| *A61K 8/73* | (2006.01) |
| *A61K 8/02* | (2006.01) |
| *A61K 8/34* | (2006.01) |
| *A61K 8/81* | (2006.01) |
| *A61Q 1/02* | (2006.01) |
| *C08L 67/04* | (2006.01) |
| *C08L 3/02* | (2006.01) |
| *C08L 23/08* | (2006.01) |
| *C08L 31/04* | (2006.01) |
| *C08L 29/04* | (2006.01) |
| *C08L 77/02* | (2006.01) |

(52) U.S. Cl.
CPC .............. *A61K 8/732* (2013.01); *A61K 8/025* (2013.01); *A61K 8/345* (2013.01); *A61K 8/8129* (2013.01); *A61Q 1/02* (2013.01); *C08L 3/02* (2013.01); *C08L 23/0869* (2013.01); *C08L 29/04* (2013.01); *C08L 31/04* (2013.01); *C08L 67/04* (2013.01); *C08L 77/02* (2013.01)

(58) Field of Classification Search
None
See application file for complete search history.

(56) References Cited

U.S. PATENT DOCUMENTS

| | | | |
|---|---|---|---|
| 6,472,497 B2 | 10/2002 | Loercks et al. | |
| 2002/0044968 A1* | 4/2002 | van Lengerich | ........ B29B 7/482 424/469 |
| 2004/0146540 A1 | 7/2004 | Ueda et al. | |

FOREIGN PATENT DOCUMENTS

| | | |
|---|---|---|
| WO | WO-00/17270 A1 | 3/2000 |
| WO | WO-2013/041561 A1 | 3/2013 |

OTHER PUBLICATIONS

Chinese Office Action issued in CN Appln. 201780007233.6 dated Jul. 28, 2020.

* cited by examiner

Primary Examiner — Nicole P Babson
(74) Attorney, Agent, or Firm — Polsinell PC

(57) ABSTRACT

This invention relates to the use of microgranules comprising destructurized starch in a complexed form as abrasive and/or structuring agents in cosmetic, dermatological, detergent and cleansing formulations.

4 Claims, No Drawings

USE OF COMPOSITIONS COMPRISING DESTRUCTURIZED STARCH IN A COMPLEXED FORM AS ABRASIVES AND/OR STRUCTURING AGENTS

CROSS REFERENCE TO RELATED APPLICATIONS

This application is the National Phase of Application No. PCT/EP2017/050972 filed Jan. 18, 2017, which claims priority to Application No. 10201600004478 filed in Italy on Jan. 19, 2016 under 35 U.S.C. § 119. The entire contents of each application are hereby incorporated by reference.

This invention relates to the use of microgranules comprising destructurized starch in a complexed form as abrasives and/or structuring agents in cosmetic, dermatological, detergent and cleansing formulations.

The abrasive and/or structuring agents are plastics microgranules (otherwise known as microbeads) which have long been used to achieve an abrasive effect or having an aesthetic-structuring function in various sectors of industry and in a wide range of products, such as for example cosmetic, dermatological, detergent and cleansing formulations.

Conventional microbeads are mainly based on polyethylene and/or polyamides and because of the very long degradation times of these polymers they may give rise to risks of a build-up of plastics microparticles in the environment, and in ocean, sea, river and lake waters in particular. Said plastics microparticles thus contribute to the phenomenon commonly known as "micropollution", that is the accumulation of plastics microfragments having very long decomposition times which are ingested by fish and marine mammals, and progressively accumulate in the food chain.

In light of the increasingly manifest harmfulness of this phenomenon, many initiatives with a view to discouraging and progressively eliminating the use of conventional microbeads in various types of products, including cosmetic products in particular, because of their adverse environmental impact, have been initiated at national level in many countries, as well as at international level.

There is therefore particular interest in various sectors of industry in identifying an alternative to conventional microbeads, to overcome the problems set out above.

Starting from this technical problem it has now been surprisingly found that it is possible to obtain performance during use which is wholly similar to that which can be achieved using conventional microbeads at costs which, if not lower, are at least comparable to those of conventional ones, using compositions comprising destructurized starch in a complexed form, which also have the advantage of being quickly biodegradable, and therefore do not cause micropollution.

This invention therefore relates to the use as an abrasive and/or structuring agent of microgranules comprising destructurized starch in a complexed form with polymers containing hydrophilic groups intercalated with hydrophobic sequences, which are particularly suitable for cosmetic, dermatological, detergent and cleansing formulations.

The term "structuring agent" as used in the present application means an ingredient able to improve the softness, smoothness, absorption rate and film-forming effect when added to aqueous or lipophilic formulations, such as emulsions. Alternatively, the term "structuring agent" as used in the present application means an ingredient able to improve and the gliding effect, smoothness and matt effect when added to anhydrous formulations. These properties are tested through sensory analysis.

The use of destructurized starch in a complexed form with polymers containing hydrophilic groups intercalated with hydrophobic sequences in fact makes it possible to obtain microgranules having an abrasive and/or structuring action in the form of spheroidal particles of diameter preferably between 1 and 1000 μm, which cannot otherwise be obtained, for example, by using starch still having its native granular structure or in any event a starch which is not in a complexed form.

In the meaning of this invention, by destructurized starch is in fact meant a starch of any type which has lost its native granular structure. As far as the native granular structure of the starch is concerned, this can advantageously be identified by means of phase contrast optical microscopy. In one particular preferred embodiment of this invention, the destructurized starch is a starch which has completely lost its native granular structure, also known as "completely destructurized starch".

Destructuring of the starch is advantageously carried out in any equipment which is capable of providing the temperature, pressure and shear force conditions suitable for destroying the native granular structure of the starch. Conditions suitable for obtaining complete destructuring of the starch are for example described in patents EP-0 118 240 and EP-0 327 505. Advantageously the starch is destructurized by means of an extrusion process at temperatures between 110 and 250° C., preferably 130-180° C., preferably at pressures between 0.1 and 7 MPa, preferably 0.3-6 MPa, and preferably providing a specific energy of more than 0.1 kWh/kg during the extrusion.

In the meaning of this invention, by destructurized starch in a complexed form with polymers containing hydrophilic groups intercalated with hydrophobic sequences is meant a destructurized starch which has formed one or more supramolecular structures which can be determined in an X-ray spectrometer (Cu $K_\alpha$ X-radiation with λ=1.5416 Å units), in the form of one or more crystalline forms which can be associated with one or more of the diffraction peaks of those listed below.

| Crystalline form | $V_H$ (2θ) | $V_A$ (2θ) | $E_H$ (2θ) |
|---|---|---|---|
| | 7.4 (±0.3) | 7.7 (±0.3) | 7.0 (±0.2) |
| | 12.8 (±0.2) | 13.5 (±0.4) | 12.0 (±0.3) |
| | 16.7 (±0.2) | 15.7 (±0.1) | 13.1 (±0.3) |
| | 18.3 (±0.2) | 17.6 (±0.1) | 18.2 (±0.4) |
| | 19.7 (±0.3) | 19.3 (±0.2) | 24.9 (±0.2) |
| | 22.2 (±0.2) | 20.8 (±0.2) | |
| | 24.9 (±0.2) | 23.7 (±0.1) | |
| | | 26.4 (±0.1) | |
| | | 27.5 (±0.1) | |
| | | 28.6 (±0.1) | |

In a preferred embodiment the microgranules according to this invention comprise, with respect to the total weight of components i-iv:
i. 30-80% of destructurized starch;
ii. 20-70% of polymers containing hydrophilic groups intercalated with hydrophobic sequences;
iii. 0-25% of plasticizers;
iv. 0-50% of water.

The starch which can be used for preparation of the destructurized starch according to this invention is preferably selected from native starch (such as for example maize starch, potato starch, rice starch, tapioca starch), oxidized starch, dextrinized starch, etherified starch (such as preferably starch ethoxylate, starch silyl ethers), starch esters (such as preferably starch hydroxypropylate, starch acetate), and mixtures thereof. Preferably the starch used for preparation of the destructurized starch is native starch.

In one embodiment this invention relates to use of microgranules comprising one or more "silyl ethers of destructurized starch" as an abrasive and/or structuring agent, and by this term are meant destructurized starches in which at least one oxygen atom of the destructurized starch is covalently bound to at least one silicon atom and/or to at least one compound containing silicon.

As far as the compounds containing silicon are concerned, these are preferably selected from the group comprising organosilanes, including organodisilanes, organotrisilanes, organopolysilanes, halosilanes, including di-, tri- and polyhalosilanes, silanols, including di-, tri- and polysilanols, and silazanes, including di-, tri- and polysilazanes. More preferably the silicon-containing compounds are selected from organosilanes, even more preferably from those having a general formula selected from:

$$(RO)_3SiC_nH_{2n+1} \quad (I)$$

$$(RO)_3SiC_nH_{2n}X \quad (II)$$

$$(RO_3SiC_nH_{2n}S_mY \quad (III)$$

$$(RO)_3SiC_nH_{2n}S_mC_nH_{2n}Si(OR)_3 \quad (IV)$$

in which R represents an alkyl group having from 1 to 4 carbon atoms, the R being the same or different from each other;

"n" represents a whole number from 1 to 12;

"m" represents a whole number from 1 to 6;

X represents a mercaptan group, an amine group, a vinyl group, a nitroso group, an imide group, a chlorine atom or an epoxy group;

Y represents a cyano group, an N,N-dimethyl thiocarbamoyl group, a mercaptobenzotriazole group, or a methacrylate group.

Organosilanes which contain no sulfur are particularly preferred.

As far as the silyl ethers of destructurized starch are concerned, these can be obtained by means of a single stage process or in several stages. In a first preferred embodiment, the silyl ethers of destructurized starch are obtained by subjecting one or more silyl ethers of starch to temperature, pressure and shear force conditions suitable for destroying the native granular structure of the starch, in accordance with the teachings shown above in relation to the destructuring process.

Alternatively, the silyl ethers of destructurized starch are preferably obtained by mixing the already destructurized starch with at least one silicon-containing compound at temperatures of between 110 and 250° C., preferably 130-180° C. Mixing may take place in any equipment suitable for the purpose, preferably in a static mixer or extruder, more preferably in an extruder. During the preparation of the silyl ethers of destructurized starch according to this invention the silicon-containing compounds may be dosed in excess with respect to the starch or in any event not caused to react completely with the latter so that the silyl ethers of destructurized starch according to the present invention may advantageously contain between 1 and 20% by weight of at least one compound containing silicon, preferably organosilanes, halosilanes, silanols, and silazanes which are not bound to an oxygen atom of the starch. More preferably, the said silicon compound which is not attached to an oxygen atom of the starch is an organosilane.

As far as the polymers containing hydrophilic groups intercalated with hydrophobic sequences are concerned, these are advantageously selected from:
 i. polyvinyl alcohols having a degree of hydrolysis between 10 and 100%, preferably between 70 and 99%;
 ii. vinyl alcohol/vinyl acetate block copolymers;
 iii. polyvinyl acetate in dry form or in a form emulsified in water;
 iv. copolymers of ethylene with vinyl alcohol, vinyl acetate, acrylic acid, methacrylic acid, crotonic acid, itaconic acid, maleic anhydride, glycidyl methacrylate and mixtures thereof;
 v. 6-6, 6-9 or 12 aliphatic polyamides, aliphatic polyurethanes, aliphatic and aliphatic/aromatic polyesters, polyurethane/polyamide, polyurethane/polyether, polyurethane/polyester, polyamide/polyester, polyamide/polyether, polyester/polyether, polyurea/polyester, polyurea/polyether, polylactic acid, polyglycolic acid, polycaprolactone/urethane random or block copolymers, in which the molecular weight of the polycaprolactone blocks is between 300 and 3000.

Mixtures of the said polymers may also be used.

Among the polymers containing hydrophilic groups intercalated with hydrophobic sequences, those preferred are copolymers of ethylene with vinyl alcohol and/or acrylic acid, the polyvinyl alcohols having a degree of hydrolysis from 10 to 100%, polyvinyl acetates in dry form or in a form emulsified in water, vinyl alcohol/vinyl acetate block copolymers and mixtures thereof.

Of these those particularly preferred are copolymers of ethylene with vinyl alcohol and/or acrylic acid and polyvinyl alcohols having a degree of hydrolysis between 10 and 100%. Even more preferably polyvinyl alcohols having a degree of hydrolysis between 70 and 99% are used as polymers containing hydrophilic groups intercalated with hydrophobic sequences.

In the case of copolymers of ethylene with vinyl alcohol, the latter preferably contain 20-50% in moles of ethylene units.

In the case of ethylene copolymers with acrylic acid, these preferably contain 70-99% by weight of ethylene units.

As far as the plasticizers are concerned, these are preferably selected from polyols having from 2 to 22 carbon atoms. Among the polyols those preferred are polyols having from 1 to 20 hydroxyl groups containing from 2 to 6 carbon atoms, their ethers, thioethers and organic and inorganic esters. Examples of polyols are glycerine, diglycerol, polyglycerol, pentaerythritol, polyglycerol ethoxylate, ethylene glycol, polyethylene glycol, 1,2-propanediol, 1,3-propanediol, 1,4-butanediol, neopentylglycol, sorbitol monoacetate, sorbitol diacetate, sorbitol monoethoxylate, sorbitol diethoxylate, and mixtures thereof. In a preferred embodiment, the plasticizers comprise glycerol or a mixture of plasticizers comprising glycerol, more preferably comprising between 2 and 90% by weight of glycerol with respect to the total weight of plasticizers.

As far as the water is concerned, this may also be that naturally present in the starch. The microgranules according to this invention may also comprise other additives, for example fillers, dispersants, cross-linking agents, surfactants, anti-foaming agents, suspensory agents, thickeners, preservatives, pigments and colouring agents in addition to components i-iv.

As far as the fillers are concerned, these may be inorganic and/or organic. Examples of particularly preferred inorganic fillers are: talc, clays, silica, mica, kaolin, titanium dioxide and wollastonite. The preferred organic fillers are those deriving from raw materials of renewable origin, such as for example cellulose fibres.

The surfactants are advantageously selected from anionic, cationic and non-ionic surfactants.

The cationic surfactants generally comprise a large volume cation often containing a long alkyl chain (for example a quaternary ammonium, a phosphonium or sulfonium salt). In most cases the anion is the chloride, sulfate or nitrate ion. The anionic surfactants generally comprise alkyl, aryl, alkylaryl, styryl, di- or tristyryl sulfonates, sulfates, phosphates, phosphonates, dithiocarbamates, or carboxylates generally neutralised with alkali or alkaline earth metals, amines and alkanolamines.

Examples of non-ionic surfactants comprise products belonging to the classes of polyethoxylate esters and ethers, alkyl polyglucosides, sorbitol and saccharose derivatives, fatty acid esters or amides, fatty amine mono and diglycerides, ethoxylated alkylphenols, di- or tristyrylphenylethoxylates, or etho-propoxylate block copolymers.

Examples of anti-foaming agents include silicone anti-foaming agent and salts of fatty acids.

Pigments and colouring agents or colour stabilisers may also be added if necessary, for example titanium dioxide, clays, calcium carbonate, talc, mica, silica, silicates, iron oxides and hydroxides, carbon black and magnesium oxide.

The microgranules comprising destructurized starch in a complexed form with polymers containing hydrophilic groups intercalated with hydrophobic sequences according to this invention may be prepared by a process which comprises one or more stages of mixing the components, the said mixing being preferably carried out by means of extrusion. Extruders which are suitable for use for the mixing stages according to this invention are both mono twin screw extruders, preferably provided with screws having profiles with a high mixing capacity (e.g. the presence of "reverse" elements).

In a first embodiment, the microgranules according to this invention are prepared by means of a process which comprises a single stage of mixing the components, and in which the destructuring of the starch takes place in the presence of the polymers containing hydrophilic groups intercalated with hydrophobic sequences, preferably in the presence of one or more plasticizers such as those described above and/or water, the said water advantageously being that naturally present in the starch, by means of an extrusion process preferably at temperatures of between 110 and 250° C. and more preferably between 130 and 210° C. and providing a specific energy of preferably more than 0.1 kWh/kg during the said extrusion.

In a preferred embodiment of the said process comprising a single mixing stage, the microgranules according to this invention can then be obtained by means of a process providing for one stage of mixing in which:
  a. a composition comprising 20 to 90% by weight of at least one native starch, from 10 to 80% by weight of at least one polymer containing hydrophilic groups intercalated with hydrophobic sequences, from 0 to 40% by weight of one or more plasticizers preferably comprising at least 2-90% by weight of glycerol with respect to the total weight of plasticizers, from 0 to 40% by weight of water, is extruded at a temperature of between 110 and 250° C., preferably between 130 and 210° C., and providing specific energy preferably above 0.1 kWh/kg.

In another embodiment the polymers containing hydrophilic groups intercalated with hydrophobic sequences and any other components may also be added subsequently to destructuring of the starch. In accordance with this embodiment the microgranules according to this invention can then be obtained by means of a process providing two mixing stages in which:
  a. at least one native starch is extruded preferably in the presence of 0-40% by weight with respect to the weight of the native starch of one or more plasticizers preferably comprising at least 2-90% by weight of glycerol with respect to the total weight of the plasticizers at a temperature of between 110 and 250° C., preferably 130-180° C. and providing a specific energy of preferably above 0.1 kWh/kg, and
  b. a composition comprising 30-90% by weight of the destructurized starch obtained in stage a, 10-70% by weight of at least one polymer containing hydrophilic groups intercalated by hydrophobic sequences, 0-40% by weight of one or more plasticizers preferably comprising at least 2-90% by weight of glycerol with respect to the total weight of the plasticizers, 0-40% by weight of water is extruded at a temperature of between 110 and 250° C., preferably 130-210° C., and providing a specific energy of preferably above 0.1 kWh/kg.

After the components have been mixed, preparation of the microgranules according to this invention preferably provides for grinding treatment to obtain spheroidal particles of diameter between 1 and 100 µm, preferably between 1 and 60 µm.

The said grinding treatment provides a step of cryogenic grinding of the complexed starch in order to pre-reduce the dimensions of the particles to a diameter of less than 1 mm and subsequent jet-mill grinding in order to obtain the desired size.

The diameter of the spheroidal particles is determined using a laser granulometer in accordance with standard ISO 13320.

Preferably the microgranules according to the present invention are used as abrasive and/or structuring agents in cosmetic, dermatological, detergent and cleansing formulations.

According to another embodiment, the present invention relates to the use of microgranules in laser sintering applications.

The cosmetic, dermatological, detergent and cleansing formulations preferably comprise up to 20% by weight, more preferably from 1 to 10% by weight, even more preferably from 2 to 5% by weight, of microgranules comprising destructurized starch in a complexed form with polymers containing hydrophilic groups intercalated with hydrophobic sequences as an abrasive and/or structuring agent according to this invention, the said percentage relating to the total weight of the respective formulations.

Preferably, thanks to the use of microgranules according to this invention, the cosmetic, dermatological, detergent and cleansing formulations have optimum sensory properties in terms of flowability, and/or optimum stability properties for example determined in terms of not significant variations of pH, viscosity, colour, smell or appearance, even after six months.

The cosmetic, dermatological, detergent and cleansing formulations according to this invention preferably take the form of fluids, gels, foams, sprays, lotions or creams. Said formulations are preferably formulated in the form of aqueous or lipophilic formulations, such as emulsions (e.g. base creams and foundations), solutions or dispersions, or anhydrous formulations (e.g. lipsticks). The formulations according to the present invention are preferably in the form of water-in-oil and oil-in-water emulsions.

The microgranules according to this invention may be added to the said formulations in any of the ways known to those skilled in the art, in the form of aqueous dispersion.

The said formulations may also contain other additives and auxiliaries normally used in the corresponding fields of application, for example oils, waxes, surfactants, suspensory agents, preservatives, emulsifiers, co-emulsifiers, dispersants, surfactants, polymers, anti-foaming agents, solubilising agents, stabilisers, film-forming agents, thickening agents, gelling agents, emollients, disinfectants, active principles, astringents, deodorants, sun filters, antioxidants, oxidants, humectants, solvents, colouring agents, pigments, texturing agents, perfumes, opacifiers and/or silicones. In particular, plant health products also comprise one or more phytopharmaceuticals.

In a preferred embodiment the microgranules according to this invention have a biodegradability of at least 55%, preferably 60%, more preferably 70% as determined according to Standard EN13432.

In another preferred embodiment the microgranules according to this invention are biodegradable when composted in the meaning of Standard EN13432.

The invention will now be described with some Examples which are to be understood to be of an illustrative nature and not limiting the invention.

Example 1

49.5 parts of native maize starch (containing 12% by weight of water), 32.2 parts of polyvinyl alcohol having a degree of hydrolysis of 88%, 7 parts of glycerine and 11.2 parts of water were fed to an TSA twin-screw extruder set in accordance with the following operating parameters:
Thermal profile
Feed zone (° C.): 60
Extrusion zone (° C.): 120-200×4-110-90
Throughput (kg/h)=3
SME (specific energy) (kWh/kg)=0.267

The composition so obtained was ground up at 25° C. and sieved to a particle size <250 µm and analysed in a Philips X'Pert θ/2θ X-ray spectrometer with Bragg-Brentano geometry using Cu $K_\alpha$ X-ray radiation with $\lambda$=1.5416 Å and a power of 1.6 kW. The angular range used was from 5 to 60° (2θ) in steps of 0.03° (2θ) and an acquisition time of 2 seconds per step.

Analysis of the spectrum revealed the presence of diffraction peaks at 2θ=12.7-16.5-18.2-19.4-22.0 indicating formation of the complex between the starch and polyvinyl alcohol ($V_H$ form).

The composition was analysed using a Leitz Wetzlar Orthoplan model phase contrast optical microscope adjusted to the following parameters:
Magnification 400×
EF 40/0.65 Phaco 2 objective
Phase ring no. 5

The composition showed that no residues of granular structure which could be attributed to the starch were present, thus revealing the destructurized nature of the starch.

The composition was then ground by grinding in a pin crusher in the presence of liquid nitrogen yielding a powder having dimensions <1 mm. The said powder was further ground by means of jet-mill technology thus obtaining two types of microgranules in the form of spheroidal particles having a mean diameter of 9 microns (Dv90=16 microns) and 12 microns (Dv90=21 microns).

Example 2

56.3 parts of native maize starch (containing 12% by weight of water), 24.8 parts of polyethylene acrylic acid containing 20% by weight of acrylic acid, 7.9 parts of glycerine and 10.1 parts of water were fed to an OMC twin-screw extruder set in accordance with the following operating parameters:
Thermal profile
Feed zone (° C.): 60
Extrusion zone (° C.): 145-170-180×4-150×2
Throughput (kg/h)=40
SME (specific energy) (kWh/kg)=0.232

The composition so obtained was ground up at 25° C. and sieved to a particle size <250 µm and analysed in a Philips X'Pert θ/2θ X-ray spectrometer with Bragg-Brentano geometry using Cu $K_\alpha$ X-ray radiation with $\lambda$=1.5416 Å and a power of 1.6 kW. The angular range used was from 5 to 60° (2θ) in steps of 0.03° (2θ) and an acquisition time of 2 seconds per step.

Analysis of the spectrum revealed the presence of diffraction peaks at 2θ=6.8-11.8-13.1-18.1-20.7 indicating formation of the complex between the starch and the polyethylene acrylic acid ($E_H$ and $V_A$ forms).

The composition was analysed using a Leitz Wetzlar Orthoplan model phase contrast optical microscope adjusted to the following parameters:
Magnification 400×
EF 40/0.65 Phaco 2 objective
Phase ring no. 5

The composition showed that no residues of granular structure which could be attributed to the starch were present, thus revealing the destructurized nature of the starch.

The composition was then ground by grinding in a pin crusher in the presence of liquid nitrogen yielding a powder having dimensions <1 mm. The said powder was further ground by means of jet-mill technology thus obtaining two types of microgranules in the form of spheroidal particles having a mean diameter of 9 microns (Dv90=16 microns) and 12 microns (Dv90=21 microns).

The microgranules were subsequently used as a replacement for conventional microbeads to produce some cosmetic formulations, for example base cream (Examples 3-6) and foundation (Examples 7-10).

Examples 3 (Comparative), 4 (Comparative), 5, 6: Base Cream Formulations

Different base cream formulations were produced and the compositions are reported in Table 1. For each cosmetic formulation, the ingredients are listed according to INCI nomenclature, and the amount of each ingredient is referred to the total weight of the formulation.

TABLE 1

| Phase | INCI name | Composition % wt | | | |
|---|---|---|---|---|---|
| | | Example 3 (comparative) | Example 4 (comparative) | Example 5 | Example 6 |
| A | Aqua | 82.80 | 80.80 | 80.80 | 80.80 |
| | Disodium EDTA | 0.10 | 0.10 | 0.10 | 0.10 |
| | Chlorophenesin | 0.30 | 0.30 | 0.30 | 0.30 |
| B | Peg-8 Stearate, CetearylEthylhexanoate, Glyceryl Stearate, StearylHeptanoate, CetylAlcohol, Butyl Stearate, Olive Glycerides, StearylCaprylate, CetylPalmitate, SorbitanSesquioleate, Stearic Acid, Aqua, Tocopherol, Potassium Hydroxide | 10.00 | 10.00 | 10.00 | 10.00 |
| | Triolein, Glyceryl Dioleate | 6.00 | 6.00 | 6.00 | 6.00 |
| | TocopherylAcetate | 0.50 | 0.50 | 0.50 | 0.50 |
| | O-cymen-5-ol | 0.10 | 0.10 | 0.10 | 0.10 |
| C | Parfum | 0.20 | 0.20 | 0.20 | 0.20 |
| D | Nylon-12 | — | 2.00 | — | — |
| | Microgranules according to Example 1 with Dv90 = 16 microns | — | — | 2.00 | — |
| | Microgranules according to Example 1 with Dv90 = 21 microns | — | — | — | 2.00 |

Manufacturing Method the components of Phase A and Phase B were separately heated at 65° C. under stirring. Subsequently, Phase B was added to Phase A under mixing and maintained under this condition for 5 minutes. After cooling down to room temperature, Phase C and Phase D were added under stirring to the mixture.

The stability of base cream formulations according to Examples 3-6 was tested for 6 months at 25° C. (Table 2). No significant variations of Colour, Smell, Appearance, pH, Viscosity were noticed, thus confirming the stability of all the formulations.

Viscosity was measured by means of a Brookfield viscometer (RV) equipped with spindle n. 4 at 50 rpm and at 25° C.

TABLE 2

| | Example 3 (comparative) | | Example 4 (comparative) | | Example 5 | | Example 6 | |
|---|---|---|---|---|---|---|---|---|
| | | | 6 | | 6 | | 6 | |
| | beginning | 6 months | beginning | months | beginning | months | beginning | months |
| colour | conform | conform | conform | conform | conform | conform | conform | conform |
| smell | conform | conform | conform | conform | conform | conform | conform | conform |
| appearance | conform | conform | conform | conform | conform | conform | conform | conform |
| pH | 6.39 | 6.22 | 6.23 | 6.16 | 6.26 | 6.18 | 6.25 | 6.09 |
| Viscosity mPas (s = 4; 50 rpm) | 1180 | 1190 | 1060 | 1060 | 1200 | 1210 | 1100 | 1090 |

The formulations prepared according to examples 3-6 were tested in terms of their softness, smoothness, greasiness, stickiness, film-forming and absorption rate by a panel of 20 volunteers (both men and women). The sensory analyses, determined 3 minutes after the application, were classified according to the following scale:
1=absolutely not good
2=not good
3=sufficiently good
4=good
5=very good.
The results are reported in Table 3.

TABLE 3

PANEL TEST

| Example | Softness | Smoothness | Greasiness | Stickiness | Film-forming | Absorption rate |
|---|---|---|---|---|---|---|
| 3 (comparative) | 4 | 4 | 5 | 5 | 3 | 3 |
| 4 (comparative) | 5 | 4 | 5 | 5 | 4 | 5 |
| 5 | 5 | 5 | 5 | 5 | 5 | 5 |
| 6 | 5 | 5 | 5 | 5 | 5 | 5 |

3 minutes after the application, the base cream formulations of the invention (Examples 5-6) showed improved Smoothness and Film-forming effect with respect to that comprising Nylon 12 (comparative Example 4), and a general improvement with respect to the basic formulation (comparative Example 3).

EXAMPLES 7 (COMPARATIVE), 8 (COMPARATIVE), 9, 10: FOUNDATION FORMULATIONS

Different foundation formulations were produced and the compositions are reported in Table 4.

TABLE 4

| | | Composition % wt | | | |
|---|---|---|---|---|---|
| Phase | INCI name | Example 7 (comparative) | Example 8 (comparative) | Example 9 | Example 10 |
| A | Aqua | 66.25 | 62.25 | 62.25 | 62.25 |
| | Glycerin | 4.00 | 4.00 | 4.00 | 4.00 |
| | Sodium Chloride | 1.00 | 1.00 | 1.00 | 1.00 |
| | Chlorophenesin | 0.30 | 0.30 | 0.30 | 0.30 |
| B | IsodecylNeopentanoate | 3.00 | 3.00 | 3.00 | 3.00 |
| | Triolein, Glyceryl Dioleate | 2.00 | 2.00 | 2.00 | 2.00 |
| | C15-19 Alkane | 1.50 | 1.50 | 1.50 | 1.50 |
| | Cyclopentasiloxane | 3.00 | 3.00 | 3.00 | 3.00 |
| | Isotridecyl Isononanoate | 4.00 | 4.00 | 4.00 | 4.00 |
| | CetylPEG/PPG-10/1 Dimethicone | 0.70 | 0.70 | 0.70 | 0.70 |
| | C10-18 Triglycerides | 2.00 | 2.00 | 2.00 | 2.00 |
| | Cyclopentasiloxane, DimethiconeCrosspolymer | 2.00 | 2.00 | 2.00 | 2.00 |
| | O-cymen-5-ol | 0.10 | 0.10 | 0.10 | 0.10 |
| C | Titanium Dioxide, Cyclopentasiloxane, PEG/PPG-18/18 Dimethicone, Isopropyl Titanium Triisostearate, TriethoxysilylethylPolydimethylsiloxyethylDimethicone, DisteardimoniumHectorite, TocopherylAcetate | 7.00 | 7.00 | 7.00 | 7.00 |
| | Iron Oxides (C.I.77492), Cyclopentasiloxane, PEG/PPG-18/18 Dimethicone, Isopropyl Titanium Triisostearate, Triethoxysilylethyl Polydimethylsiloxyethyl Dimethicone, Disteardimonium Hectorite, Tocopheryl Acetate | 2.20 | 2.20 | 2.20 | 2.20 |

TABLE 4-continued

| | | Composition % wt | | | |
|---|---|---|---|---|---|
| Phase | INCI name | Example 7 (comparative) | Example 8 (comparative) | Example 9 | Example 10 |
| | Iron Oxides (C.I.77491), Cyclopentasiloxane, PEG/PPG-18/18 Dimethicone, Isopropyl Titanium Triisostearate, Triethoxysilylethyl Polydimethylsiloxyethyl Dimethicone, Disteardimonium Hectorite, Tocopheryl Acetate | 0.70 | 0.70 | 0.70 | 0.70 |
| | Iron Oxides (C.I.77499), Cyclopentasiloxane, PEG/PPG-18/18 Dimethicone, Isopropyl Titanium Triisostearate, Triethoxysilylethyl Polydimethylsiloxyethyl Dimethicone, Disteardimonium Hectorite, Tocopheryl Acetate | 0.25 | 0.25 | 0.25 | 0.25 |
| D | Nylon-12 | — | 4.00 | — | — |
| | Microgranules according to Example 1 with Dv90 = 16 microns | — | — | 4.00 | — |
| | Microgranules according to Example 1 with Dv90 = 21 microns | — | — | — | 4.00 |

Manufacturing Method

Phase A was prepared at 25° C., while Phase B was heated at 80° C. Phase C was added to Phase B, and cooled down to 35° C. Subsequently Phase A was added very slowly under the turboemulsifier to the mixture of Phase B and C. The mixture was then cooled down to 25° C. and Phase D was finally added.

The stability of the foundation formulations according to Examples 7-10 was tested for 6 months at 25° C. (Table 5). No significant variations of Colour, Smell, Appearance, Viscosity were noticed, thus confirming the stability of all the formulations.

Viscosity was measured by means of a Brookfield viscometer (RV) equipped with spindle n. 4 at 50 rpm and at 25° C.

TABLE 5

| | Example 7 (comparative) | | Example 8 (comparative) 6 | | Example 9 6 | | Example 10 6 | |
|---|---|---|---|---|---|---|---|---|
| | beginning | 6 months | beginning | months | beginning | months | beginning | months |
| colour | conform | conform | conform | conform | conform | conform | conform | conform |
| smell | conform | conform | conform | conform | conform | conform | conform | conform |
| appearance | conform | conform | conform | conform | conform | conform | conform | conform |
| Viscosity mPas (s = 4; 50 rpm) | 28600 | 27900 | 29000 | 28950 | 28500 | 29650 | 29700 | 29320 |

The formulations prepared according to examples 7-10 were tested in terms of their softness, smoothness, greasiness, stickiness, film-forming and absorption rate by a panel of 20 volunteers (both men and women). The sensory analyses, determined 3 minutes after the application, were classified according to the following scale:
1=absolutely not good
2=not good
3=sufficiently good
4=good
5=very good.

The results are reported in Table 6.

TABLE 6

| | | | PANEL TEST | | | |
|---|---|---|---|---|---|---|
| Example | Softness | Smoothness | Greasiness | Stickiness | Film-forming | Absorption rate |
| 7 (comparative) | 3 | 3 | 5 | 4 | 3 | 3 |
| 8 (comparative) | 4 | 4 | 4 | 4 | 4 | 3 |
| 9 | 5 | 5 | 5 | 5 | 5 | 4 |
| 10 | 5 | 5 | 5 | 5 | 5 | 4 |

The foundation formulations of the invention (Examples 9-10) showed a general improvement with respect to the basic formulation (comparative Example 7) and with respect to that comprising Nylon 12 (comparative Example 8).

In addition to the advantages reported above, the formulations containing the microgranules according to the present invention have a higher biodegradability with respect to common formulations including microgranules.

The microgranules according to the present invention were effectively used as a replacement for conventional microbeads to produce cosmetic formulations, with better performance than conventional microbeads.

The invention claimed is:

1. A composition selected from the group consisting of cosmetic, dermatological, detergent and cleansing formulations comprising, as abrasive and/or structuring agent, from 1 to 20% by weight, with respect to the total weight of the composition, of microgranules comprising destructurized starch in a complexed form with polymers containing hydrophilic groups intercalated with hydrophobic sequences, said microgranules being in the form of spheroidal particles of diameter between 1 and 100 μm, and wherein the polymers containing hydrophilic groups intercalated with hydrophobic sequences are polyvinyl alcohols having degrees of hydrolysis from 10 to 100%.

2. The composition according to claim 1, in which the said microgranules comprise, with respect to the total of components i-iv:
   i. 30-80% of destructurized starch;
   ii. 20-70% of polymers containing hydrophilic groups intercalated with hydrophobic sequences;
   iii. 0-25% of plasticizers;
   iv. 0-50% of water.

3. The composition according to claim 1, wherein the microgranules are in the form of spheroidal particles of diameter between 1 and 60 μm.

4. The composition according to claim 2, wherein the microgranules are in the form of spheroidal particles of diameter between 1 and 60 μm.

* * * * *